(12) United States Patent
Mueller et al.

(10) Patent No.: US 11,717,165 B2
(45) Date of Patent: Aug. 8, 2023

(54) DETECTION APPARATUS FOR DETERMINING A STATE OF TISSUE

(71) Applicant: KONINKLIJKE PHILIPS N.V., Eindhoven (IL)

(72) Inventors: Manfred Mueller, Eindhoven (NL); Bernardus Hendrikus Wilhelmus Hendriks, Eindhoven (NL); Gerhardus Wilhelmus Lucassen, Eindhoven (NL); Jeroen Jan Horikx, Weert (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1074 days.

(21) Appl. No.: 14/356,180

(22) PCT Filed: Oct. 30, 2012

(86) PCT No.: PCT/IB2012/056008
§ 371 (c)(1),
(2) Date: May 5, 2014

(87) PCT Pub. No.: WO2013/068885
PCT Pub. Date: May 16, 2013

(65) Prior Publication Data
US 2014/0316280 A1   Oct. 23, 2014

Related U.S. Application Data

(60) Provisional application No. 61/556,311, filed on Nov. 7, 2011.

(51) Int. Cl.
| A61B 5/00 | (2006.01) |
| A61B 18/14 | (2006.01) |
| A61B 18/00 | (2006.01) |

(52) U.S. Cl.
CPC ........ *A61B 5/0071* (2013.01); *A61B 18/1492* (2013.01); *A61B 2018/00577* (2013.01); *A61B 2018/00642* (2013.01)

(58) Field of Classification Search
CPC .............. A61B 5/0071; A61B 18/1492; A61B 2018/00642; A61B 2018/00577
See application file for complete search history.

(56) References Cited

U.S. PATENT DOCUMENTS

| 3,972,617 A | * | 8/1976 | Shibata | ..................... G01J 3/42 |
| | | | | 356/319 |
| 4,378,971 A | * | 4/1983 | Schwartz | ............... G01N 33/72 |
| | | | | 422/401 |

(Continued)

FOREIGN PATENT DOCUMENTS

| CN | 101975769 A | 2/2011 |
| WO | WO199610363 | 4/1996 |

OTHER PUBLICATIONS https://www.sciencedirect.com/topics/chemistry/fluorescence-spectrum, Treatise on Geochemistry, 2003.*

(Continued)

*Primary Examiner* — Bo Joseph Peng

(57) ABSTRACT

The invention relates to a detection apparatus (30) for determining a state of tissue. The detection apparatus (30) comprises a fluorescence spectrum providing unit (2, 3) for providing a fluorescence spectrum of the tissue, a differentiation unit (4) for generating a derivative of the fluorescence spectrum, and a tissue state determination unit (5) for determining the state of the tissue from the derivative. This allows determining the state of the tissue, even if characteristics, which are related to the state of the tissue, are only hardly visible or not visible at all in the fluorescence spectrum. The reliability of determining the state of the (Continued)

tissue, for instance, whether the tissue is cancerous or not, can therefore be improved.

13 Claims, 20 Drawing Sheets

(56) References Cited

U.S. PATENT DOCUMENTS

| | | | | |
|---|---|---|---|---|
| 4,539,180 | A | * 9/1985 | Schwartz | G01N 33/72 436/66 |
| 5,042,494 | A | 8/1991 | Alfano | |
| 5,131,398 | A | 7/1992 | Alfano et al. | |
| 5,579,773 | A | * 12/1996 | Vo-Dinh | A61B 5/0071 600/317 |
| 6,289,236 | B1 | 9/2001 | Koenig et al. | |
| 2003/0001104 | A1 | * 1/2003 | Sendai | A61B 1/00009 250/458.1 |

OTHER PUBLICATIONS

L. Baert et al., "Clinical Fluorescence Diagnosis of Human Bladder Carcinoma Following Low-Dose Photofrin Injection", Urology, vol. 41, No. 4, Apr. 1993, pp. 322-330.

R.S. Bradley et al., "A Review of Attenuation Correction Techniques for Tissue Fluorescence", J.R. Soc. Interface (2006) 3, pp. 1-13.

A.C. Croce et al., "Human Liver Autofluorescence: An Intrinsic Tissue Parameter Discriminating Normal and Diseased Conditions", Lasers in Surgery and Medicine 42 (2010, pp. 371-378.

R. Cubeddu et al., "Study of Porphyrin Fluorescence in Tissue Samples of Tumour-Bearing Mice", Journal of Photochemistry and Photobiology B: Biology 29 (1995), pp. 171-178.

R.S. Dacosta et al., "Molecular Fluorescence Excitation-Emission Matrices Relevant to Tissue Spectroscopy", Photochemistry and Photobiology, 2003, 78(4), pp. 384-392.

A.E. Desjardins et al., "Epidural Needle With Embedded Optical Fibers for Spectroscopic Differentiation of Tissue Ex-Vivo Feasibility Study", Biomedical Optics Express, vol. 2, No. 6, Jun. 1, 2011, pp. 1452-1461.

T. Dramicanin et al., "Application of Supervised Self-Organizing Maps in Breast Cancer Diagnosis by Total Synchronous Fluorescence Spectroscopy", Applied Spectroscopy, vol. 65, No. 3, 2011, pp. 293-297.

X. Li et al., "Spectral Changes of Lung Cancer Serum in the Process of Tumor Evaluation", 2011 Proceedings of the 23rd Annual EMBS International Conference, Oct. 25-28, 2001, Istanbul, Turkey, pp. 3216-3220.

S. Sommer et al., "Formation of Metal Complexes of Tumor-Localizing Porphyrins", Federation of European Biochemical Societies, vol. 172, No. 2, Jul. 1984, pp. 267-271.

* cited by examiner

DETECTION APPARATUS FOR DETERMINING A STATE OF TISSUE

CROSS-REFERENCE TO PRIOR APPLICATIONS

This application is the U.S. National Phase application under 35 U.S.C. § 371 of International Application Serial No. PCT/IB2012/056008, filed on Oct. 30, 2012, which claims the benefit of U.S. Application Ser. No. 61/556,311, filed on Nov. 7, 2011. These applications are hereby incorporated by reference herein.

FIELD OF THE INVENTION

The invention relates to a detection apparatus, a detection method and a detection computer program for determining a state of tissue. The invention relates further to an energy application apparatus, an energy application method and an energy application computer program for applying energy to tissue.

BACKGROUND OF THE INVENTION

U.S. Pat. No. 5,042,494 discloses a method and apparatus for detecting the presence of cancerous tissue using native visible luminescence. The tissue to be examined is excited with a beam of monochromatic light that causes the tissue to fluoresce over a spectrum of wavelengths. The intensity at which the excited tissue fluoresces is measured either over a spectrum or at a predetermined number of preselected wavelengths. The carcinomatoid status of the tissue in question is determined, for example, a) by determining peak wavelengths, at which maximum intensities are attained for the tissue in question, and by comparing these peak wavelengths, either visually or electronically, to peak wavelengths derived from known non-cancerous tissue, or b) by comparing the luminescence spectrum of the excited tissue with the luminescence spectrum of known non-cancerous tissue. If it has been determined that the tissue is cancerous, it can be destroyed by ablation using a beam of light from a high power laser.

In practice, it can be difficult to determine characteristics of a spectrum, which are related to a cancerous state or a healthy state of the tissue in question, because these characteristics may hardly be visible in the spectrum or not visible at all, thereby reducing the reliability of determining whether the tissue in question is cancerous or not.

SUMMARY OF THE INVENTION

It is an object of the present invention to provide a detection apparatus, a detection method and a detection computer program for determining a state of tissue, wherein the reliability of determining the state can be increased. It is a further object of the present invention to provide an energy application apparatus, an energy application method and an energy application computer program for applying energy to tissue, which use the result of the reliable determination of the state of the tissue.

In a first aspect of the present invention a detection apparatus for determining a state of tissue is presented, wherein the detection apparatus comprises:

a fluorescence spectrum providing unit for providing a fluorescence spectrum of the tissue,
a differentiation unit for generating a derivative of the fluorescence spectrum,
a tissue state determination unit for determining the state of the tissue from the derivative.

Since the differentiation unit generates a derivative of the fluorescence spectrum, wherein the tissue state determination unit determines the state of the tissue from the derivative, the state of the tissue can be determined, even if characteristics, which are related to the state of the tissue, are only hardly visible or not visible at all in the fluorescence spectrum itself. For example, these characteristics can be visible in the fluorescence spectrum only as hardly visible shoulders, which can often not reliable be detected. However, these shoulders can be reliably detectable in the derivative of the fluorescence spectrum, in particular, in the first derivative of the fluorescence spectrum. Determining the state of the tissue from the derivative increases therefore the reliability of determining the state.

The detection apparatus is preferentially adapted to determine a state of tissue which comprises a fluorophore which emits fluorescence light, after having been illuminated by excitation light. The tissue is preferentially tissue of a living being like a human being or an animal, wherein the detection apparatus can be adapted to determine whether the tissue is in a healthy state or in a cancerous state.

The fluorescence spectrum providing unit can be storing unit, in which the fluorescence spectrum is stored and from which the fluorescence spectrum can be provided, or the fluorescence spectrum providing unit can be a receiving unit for receiving the fluorescence spectrum via a data connection from, for example, a spectrometer and for providing the received fluorescence spectrum. The detection apparatus can therefore be regarded as a computing apparatus, which determines the state of the tissue based on a provided fluorescence spectrum, which might have been measured by another separate apparatus. However, preferentially the fluorescence spectrum providing unit comprises an excitation illumination unit for illuminating the tissue with excitation light for exciting the tissue for allowing the tissue to emit emission light after having been excited, and an emission light detection unit for detecting a spectrum of the emission light from the tissue. In particular, the excitation illumination unit is preferentially adapted to illuminate tissue within a living being and the emission light detection unit is preferentially adapted to detect light from the tissue within the living being. In an embodiment, the excitation illumination unit is be adapted to illuminate the tissue with excitation light having one or several wavelengths and the emission light detection unit is adapted to detect a spectrum of the emission light as the fluorescence spectrum. In another embodiment, the excitation illumination unit is adapted to illuminate the tissue with excitation light having a varying substantially single wavelength and the emission light detection unit is adapted to detect the emission light at a wavelength range, in particular, at one or more fixed wavelengths, wherein the emission light intensity detected for different wavelengths of the excitation light forms the fluorescence spectrum.

The fluorescence spectrum can be a discrete spectrum or a continuous spectrum. The discrete spectrum can comprise fluorescence intensity values at three or more wavelengths, which are used for generating the derivative of the discrete spectrum at wavelengths, at which the derivative is used for determining the state of the tissue.

The detection apparatus can comprise a probe through which the tissue within the living being can be illuminated and through which light from the tissue can be detected. The probe can be a needle, but can also be another probe, for instance, another interventional instrument like a catheter.

The probe is preferentially connected with an excitation light source and an emission light detector, in particular, a spectrometer, wherein light from the light source can be transferred from the light source through the probe to the tissue within the living being and light from the tissue within the living being can be transferred back through the probe to the detector. For transferring the light, light guides like optical fibers can be used.

It is preferred that the tissue state determination unit is adapted determine the state of the tissue based on the derivative only in the wavelength range of 600 to 700 nm. In parts of the derivative of the fluorescence spectrum, which corresponds to wavelengths being smaller than 600 nm, it is likely that very pronounced absorption characteristics like absorption peaks are present, which may be caused by, for example, blood, wherein these characteristics could reduce the reliability of determining the state of the tissue based on the derivative. Determining the state of the tissue based on the derivative only in the wavelength range of 600 to 700 nm can therefore further improve the reliability of determining the state of the tissue.

It is further preferred that the tissue state determination unit is adapted to determine whether the tissue is in a first state or in a second state, wherein the first state is related to a first wavelength and the second state is related to a second wavelength, wherein the tissue state determination unit is adapted to determine whether the tissue comprises the first state or the second state based on a first measure that depends on the derivative at wavelengths within a first wavelength range around the first wavelength and the derivative at wavelengths within a second wavelength range around the second wavelength. In particular, the state of the tissue can be determined based on the derivative at certain wavelengths only.

Preferentially, the first wavelength is related to the first state and the second wavelength is related to the second state, if characteristics of the fluorescence spectrum and/or the derivative are indicative of the respective state. In particular, the first wavelength surrounded by the first wavelength range and the second wavelength surrounded by the second wavelength range can be chosen such that they define regions of the derivative of the spectrum, in which characteristics of the derivative of the spectrum, which are indicative of the first state and the second state, respectively, are very pronounced, if the tissue is in the first state or the second state, respectively. For example, the first wavelength can correspond to a main peak of a fluorescence spectrum of a fluorophore, which is known to be present in the tissue, if the tissue is in the first state, and the second wavelength can correspond to a main peak of a fluorescence spectrum of a further fluorophore, which is present in the tissue, if the tissue is in the second state. This allows further increasing the reliability of determining the state of the tissue.

Preferentially, one of the first state and the second state represents a healthy state and the other of the first state and the second state represents a cancerous state.

The tissue state determination unit is preferentially adapted to comprise assignments between a) at least the first measure and b) the first state or the second state, and to determine whether the tissue comprises the first state or the second state based on the assignments and at least the first measure. The assignments can be determined, for example, by calibration measurements, wherein the first measure and optionally further measures are determined, while it is known, whether the tissue is in the first state or in the second state.

It is also preferred that the tissue state determination unit is adapted to determine the first measure based on at least one of
i) a first difference between a) the derivative at a wavelength, which is smaller than the first wavelength and within the first wavelength range, and b) the derivative at a wavelength, which is larger than the first wavelength and within the first wavelength range,
ii) a second difference between a) the derivative at a wavelength, which is smaller than the second wavelength and within the second wavelength range, and b) the derivative at a wavelength, which is larger than the second wavelength and within the second wavelength range. It has been found that, if the state of the tissue is determined based on this first measure, the reliability of determining the state can be further increased.

Thus, for determining the first measure it is not necessarily required to use, for example, parts of the derivative with contiguous wavelengths around the first or second wavelength, respectively, but it can be sufficient to compare the derivatives at certain wavelengths on opposite sides of the first wavelength and/or the second wavelength for determining the respective measure. These certain wavelengths on the opposite sides of the first wavelength and/or the second wavelength, respectively, can be regarded as being the border wavelengths of the first wavelength range and/or the second wavelength range, respectively, i.e. these certain wavelengths on the opposite sides can be regarded as defining the first wavelength range and/or the second wavelength range, respectively.

In an embodiment, one of the first difference and the second difference can be the first measure and the other of the first difference and the second difference can be a second measure.

In a preferred embodiment, the first wavelength is within a range of 630 to 640 nm and the second wavelength is within a range of 620 to 630 nm. In particular, the first wavelength can be 635 nm and the second wavelength can be 620 nm or 625 nm. By using these first and second wavelengths, the reliability of determining the state of the tissue can be further increased, especially if the tissue is liver or kidney tissue and if it has to be determined whether the liver or kidney tissue is in a healthy state or in a cancerous state.

It is further preferred that at least one of the first state and the second state is related to a further wavelength, wherein the tissue state determination unit is adapted to determine whether the tissue comprises the first state or the second state based on the first measure and a further measure that depends on the derivative at a wavelength within a further wavelength range around the further wavelength. The further wavelength can correspond to a secondary peak of the respective fluorescence spectrum. Considering the first measure and one or several further measures for determining the state of the tissue, can further increase the reliability of this determination.

It is also preferred that the tissue state determination unit is adapted to determine the further measure based on a difference between a) the derivative at a wavelength, which is smaller than the respective further wavelength and within the respective further wavelength range, and b) the derivative at a wavelength, which is larger than the respective further wavelength and within the respective further wavelength range. It has been found that, if the further measure is based on this difference, the reliability of determining the state of the tissue can be further increased. Thus, also for determining the further measure it is not necessarily required to use for example, a part of the derivative with contiguous wavelengths around the further wavelength, but it can be sufficient to compare the derivatives at certain wavelengths on opposite sides of the respective further wavelength for determining the respective measure.

In a preferred embodiment, the further wavelength is within a range of 675 to 685 nm or within a range of 685 to 695 nm. In particular, the further wavelength can be 680 nm or 690 nm. Especially if the tissue is liver or kidney tissue and if it should be determined, whether the liver or kidney tissue is healthy or cancerous, using this further wavelength can lead to a further increased reliability of determining the state of the tissue.

It is further preferred that the detection apparatus comprises a tissue type providing unit for providing the type of the tissue, of which the state is to be determined, wherein the tissue state determination unit is adapted to provide at least one of several predefined first measures depending on the provided tissue type. Thus, the tissue state determination unit can be adapted to determine which first measure and which optional further measure has to be applied to the derivative of the fluorescence spectrum based on the provided tissue type. For instance, the tissue state determination unit can comprise a storing unit, in which a first measure and optional further measures are assigned to different types of tissue, wherein the first measure and optional further measures to be applied in an actual measurement are determined based on the actually determined tissue type. The same detection apparatus can therefore be used for determining the state of different types of tissue.

The detection apparatus can comprise a tissue type detection illumination unit for illuminating the tissue with tissue type detection light and a tissue type detection light detection unit for detecting the tissue type detection light from the tissue, wherein the tissue type providing unit is adapted to detect the type of the tissue depending on the detected tissue type detection light. The tissue type detection illumination unit is, for example, a laser generating laser light, which can be transferred to the tissue by using, for instance, an optical fiber. The laser light is, in this example, tissue type detection light, wherein tissue type detection light, which has been influenced by the tissue by, for example, absorption, scattering and/or reflection, can be collected by at least one further optical fiber, which guides the collected light to a spectrometer for generating a tissue type detection spectrum. The tissue type detection illumination unit can also be a white light source for generating white light as the tissue type detection light. The collecting optical fiber and the spectrometer can be regarded as being the tissue type detection light detection unit. The generated tissue type detection spectrum, in particular, characteristics like peaks of the tissue type detection spectrum, can be compared with known spectra of known tissue types, in order to determine the actual type of the tissue of which the state is to be determined. This allows determining the type of the tissue, of which the state is to be detected, in a relatively simple way.

In another embodiment, the tissue type providing unit comprises a user interface for allowing a user to input the actual tissue type, wherein the tissue state determination unit is adapted to provide at least one of several predefined measures depending on the input tissue type. The user interface can be, for example, a switch, a graphical user interface, et cetera.

In a further aspect of the present invention an energy application apparatus for applying energy to tissue is presented, wherein the energy application apparatus comprises:

a detection apparatus for determining a state of tissue as defined in claim 1, and a tissue modification unit for modifying the tissue by applying energy to the tissue depending on the determined state of the tissue.

This allows modifying the tissue depending on the determined state of the tissue. The tissue modification unit is preferentially an energy application unit. The energy application unit is, for example, an ablation unit for applying ablation energy to the tissue, if the tissue has been determined to be cancerous. The energy application unit can be adapted to apply, for example, electrical energy, optical energy, ultrasound energy, heat, coldness, et cetera to the tissue for ablating the same. In particular, the tissue modification unit can be adapted to perform a photodynamic therapy.

Since the state of the tissue is determined by the detection apparatus, before energy is applied to the tissue, it can be ensured that the energy is applied to tissue having a certain state. For instance, if cancerous tissue or healthy tissue may be present, the energy application unit can be adapted such that energy is applied only to cancerous tissue, which has been determined in advance by the detection apparatus.

In a further aspect of the present invention a detection method for determining a state of tissue is presented, wherein the detection method comprises:

providing a fluorescence spectrum of the tissue, generating a derivative of the fluorescence spectrum, determining the state of the tissue from the derivative.

In a further aspect of the present invention an energy application method for applying energy to tissue is presented, wherein the energy application method comprises:

determining a state of tissue as defined in claim 12, and modifying the tissue by applying energy to the tissue depending on the determined state.

In a further aspect of the present invention a detection computer program for determining a state of tissue is presented, wherein the detection computer program comprises program code means for causing a detection apparatus as defined in claim 1 to carry out the steps of the detection method as defined in claim 12, when the detection computer program is run on a computer controlling the detection apparatus.

In a further aspect of the present invention an energy application computer program is presented, wherein the energy application computer program comprises program code means for causing an energy application apparatus as defined in claim 11 to carry out the steps of the energy application method as defined in claim 13, when the energy application computer program is run on a computer controlling the energy application apparatus.

It shall be understood that the detection apparatus of claim 1, the energy application apparatus of claim 11, the detection method of claim 12, the energy application method of claim 13, the detection computer program of claim 14 and the energy application computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
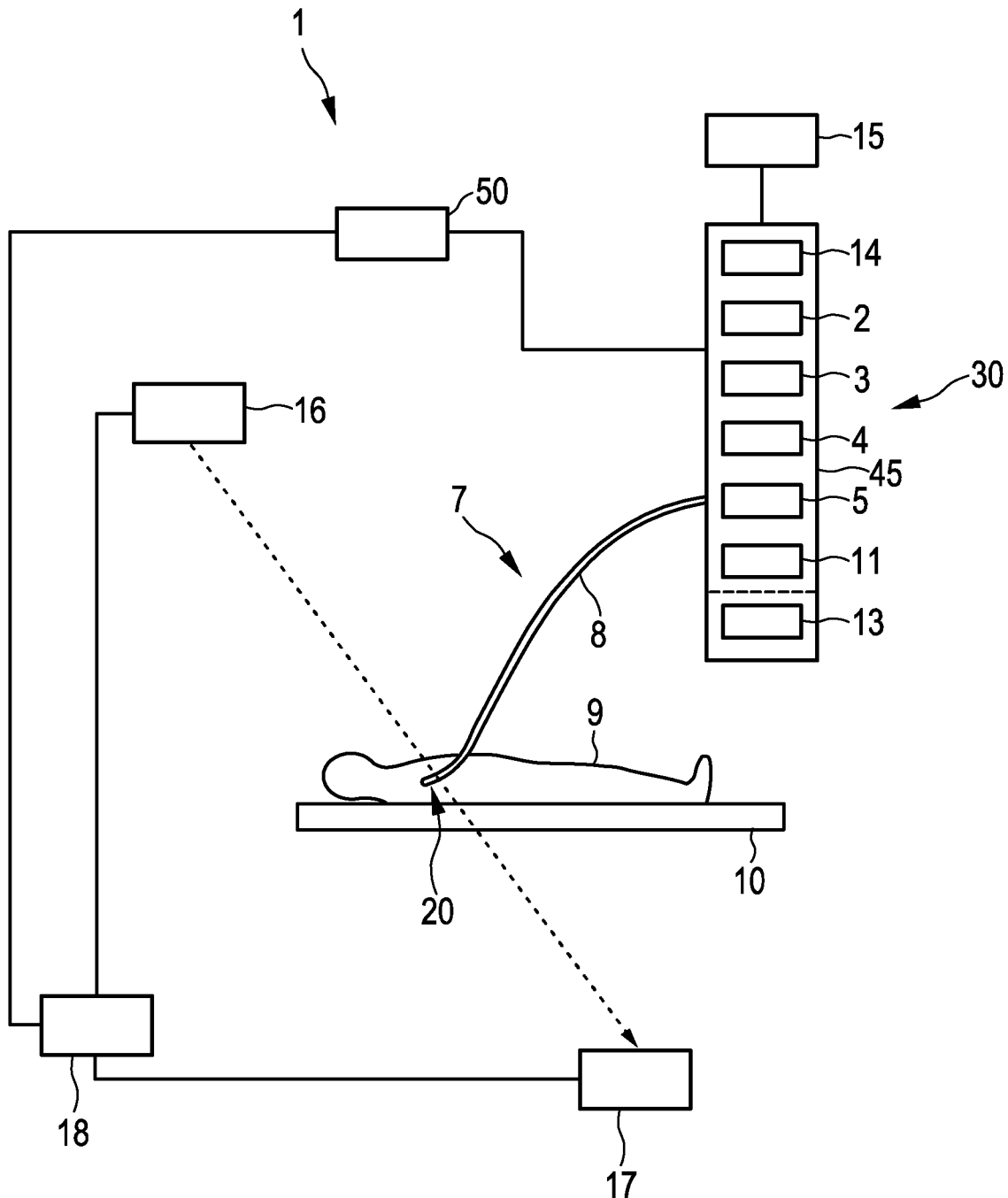
FIG. 1 shows schematically and exemplarily an embodiment of an energy application apparatus for applying energy to tissue.

FIG. 1 shows schematically and exemplarily an embodiment of an energy application apparatus 1 for applying energy to tissue. The energy application apparatus 1 comprises a detection apparatus 30 for determining a state of the tissue and a tissue modification unit 13 for modifying the tissue by applying energy to the tissue depending on the determined state.

Figure 2:
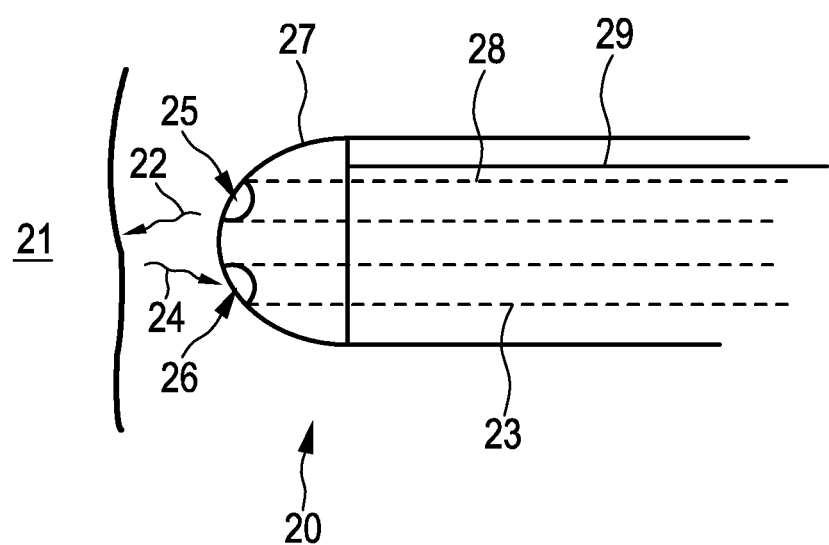
FIG. 2 shows schematically and exemplarily an embodiment of a tip of a catheter.

The detection apparatus 30 comprises an excitation illumination unit including an excitation light source 2 and at least one optical fiber within a catheter 8 for guiding excitation light generated by the excitation light source 2 via the catheter 8 to the tissue within a person 9 located on a person table 10. The tip 20 of the catheter 8, which can also be regarded as being a part of a probe 7 for probing the tissue, is exemplarily and schematically shown in more detail in FIG. 2.

The catheter tip 20 comprises a cap electrode 27 with openings 25, 26, through which excitation light 22 can leave the catheter tip 20 for exciting the tissue 21 and through which emission light 24 emitted by the tissue 21 can be collected. The excitation light is guided from the excitation light source 2 to the opening 25 via an optical fiber 28 and the collected light is guided from the opening 26 to an emission light detector 3 by an optical fiber 23. The emission light detector 3 is a spectrometer for generating an emission spectrum based on the collected emission light 24. The excitation light source 2 and the optical fiber 28 can therefore be regarded as forming an excitation illumination unit and the emission light detector 3 and the optical fiber 23 can be regarded as forming an emission light detection unit. Moreover, since the excitation illumination unit and the emission light detection unit cooperate such that they generate a spectrum and since the tissue comprises a fluorophore which emits the emission light, after having been illuminated by the excitation light, the spectrum is a fluorescence spectrum and these units can be regarded as forming a fluorescence spectrum providing unit for providing a fluorescence spectrum.

The detection apparatus 30 further comprises a differentiation unit 4 for generating a first derivative of the spectrum, and a tissue state determination unit 5 for determining the state of the tissue 21 from the derivative. In this embodiment, the tissue can have two states, i.e. it can be healthy or cancerous. The tissue state determination unit 5 can therefore be adapted to determine whether the tissue is healthy or cancerous. For performing this determination, the tissue state determination unit 5 uses preferentially the derivative only in a wavelength range of 600 to 700 nm. In particular, the tissue state determination unit 5 is adapted to determine whether the tissue 21 is in a first state, which may be one of a healthy state and a cancerous state, or in a second state, which may be the other of the healthy state and the cancerous state, wherein the first state is related to a first emission wavelength of the emission light and the second state is related to a second emission wavelength of the emission light, wherein the tissue state determination unit 5 is adapted to determine whether the tissue comprises the first state or the second state based on a first measure that depends on the derivative at wavelengths within a first wavelength range around the first wavelength, i.e., in this embodiment, around the first emission wavelength, and the derivative at wavelengths within a second wavelength range around the second wavelength, i.e., in this embodiment, around the second emission wavelength. The first and the second wavelength ranges are within the range of 600 to 700 nm.

In this embodiment, the tissue state determination unit 5 is adapted to determine the first measure as a difference between a first difference and a second difference. The first difference is the difference between a) a value of the derivative of the spectrum at a wavelength, which is smaller than the first emission wavelength and within the first wavelength range, and b) another value of the derivative of the spectrum at a wavelength, which is larger than the first emission wavelength and within the first wavelength range. The second difference is the difference between a) a value of the derivative of the spectrum at a wavelength, which is smaller than the second emission wavelength and within the second wavelength range, and b) another value of the derivative of the spectrum at a wavelength, which is larger than the second emission wavelength and within the second wavelength range. The determination of the first difference will in the following be illustrated with reference to FIGS. 3 to 6.

Figure 4:
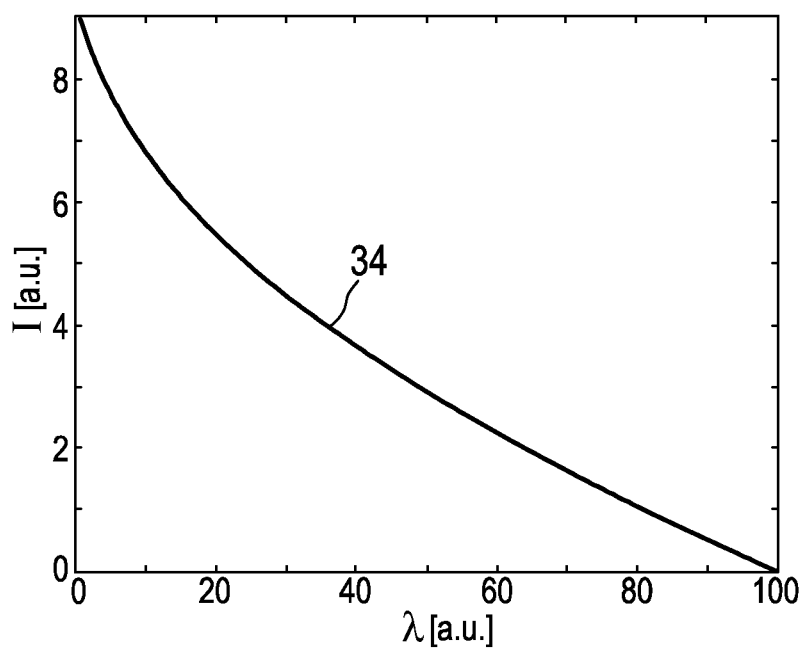
FIG. 4 shows exemplarily a background spectrum.
Figure 5:
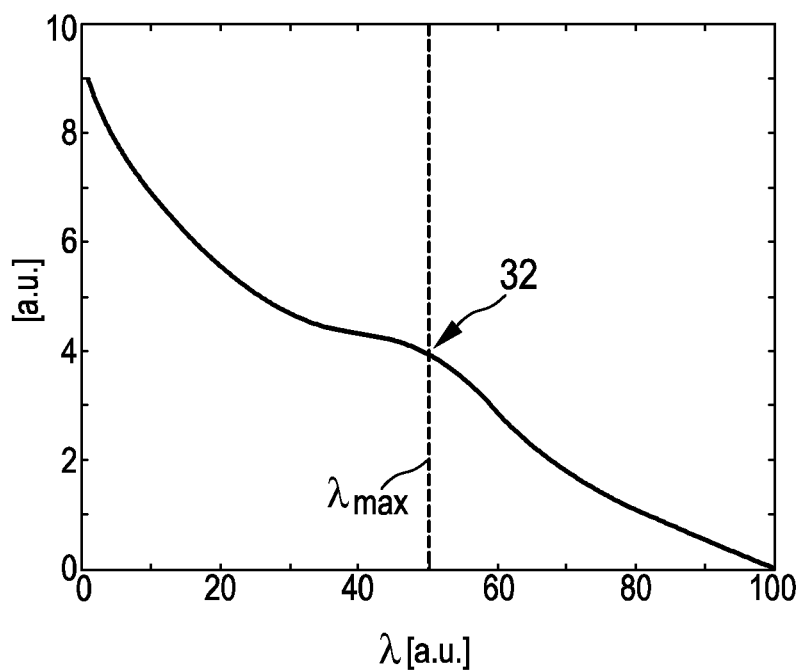
FIG. 5 shows exemplarily a combination of the spectra shown in FIGS. 3 and 4.
Figure 6:
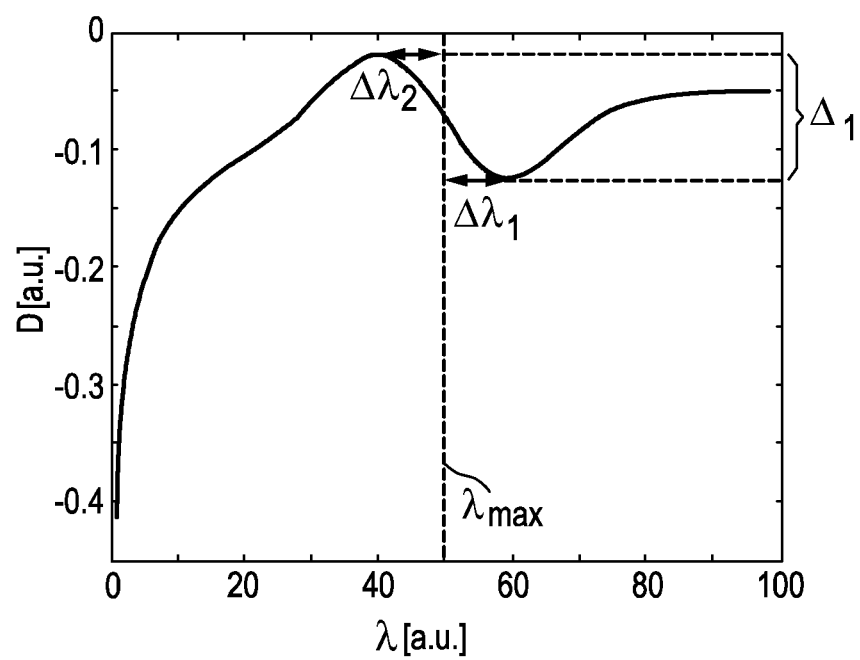
FIG. 6 shows exemplarily a first derivative of the spectrum shown in FIG. 5.

The calculation of the first difference allows reliably detecting a hardly visible shoulder 32 of the spectrum shown FIG. 5. The spectrum $I(\lambda)$ shown in FIG. 5 can be regarded as being a superposition of a peak 33 at a first emission wavelength $\lambda_{max}$ shown in FIG. 3 and a background spectrum 34 shown in FIG. 4. FIG. 6 shows schematically and exemplarily the derivative D of the spectrum shown in FIG. 5. As can been seen in FIG. 6, the first difference $\Delta_1$ is reliably detectable in FIG. 6 and can be used for calculating the first measure. In FIG. 6, the value of the derivative of the spectrum at a wavelength, which is smaller than the first emission wavelength and which within the first wavelength range, is a value of the derivative of the spectrum at the wavelength $\lambda_{max}-\Delta\lambda_2$. The other value of the derivative of the spectrum at a wavelength, which is larger than the first emission wavelength and which is within the first wavelength range, is the value at the wavelength $\lambda_{max}+\Delta\lambda_1$.

The first difference can be calculated by subtracting the values of the derivative at these two wavelengths $\lambda_{max}-\Delta\lambda_2$ and $\lambda_{max}+\Delta\lambda_1$ from each other. The second difference can be calculated accordingly.

Figure 3:
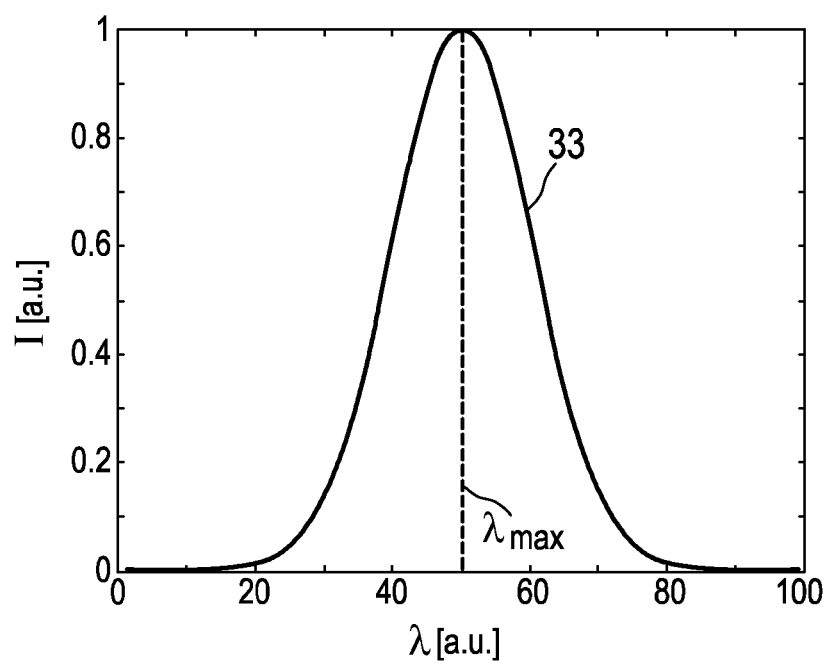
FIG. 3 shows exemplarily a peak of a spectrum.

The values $\Delta\lambda_1$ and $\Delta\lambda_2$ depend on the shape of the respective peak, in particular, on the shape of the peak shown in FIG. 3, but not on the background as shown, for instance, in FIG. 4. These values $\Delta\lambda_1$ and $\Delta\lambda_2$ can be determined in advance for a given tissue type. Thus, by taking a first derivative of a measured fluorescence spectrum and subtracting the intensity of a suitable wavelength on the right of the peak wavelength $\lambda_{max}+\Delta\lambda_1$ of the subtracted peak from a point on the left at $\lambda_{max}-\Delta\lambda_2$ of the subtracted peak wavelength, it can reliably be determined, whether a corresponding fluorophore is present in the tissue or not.

Figure 7:
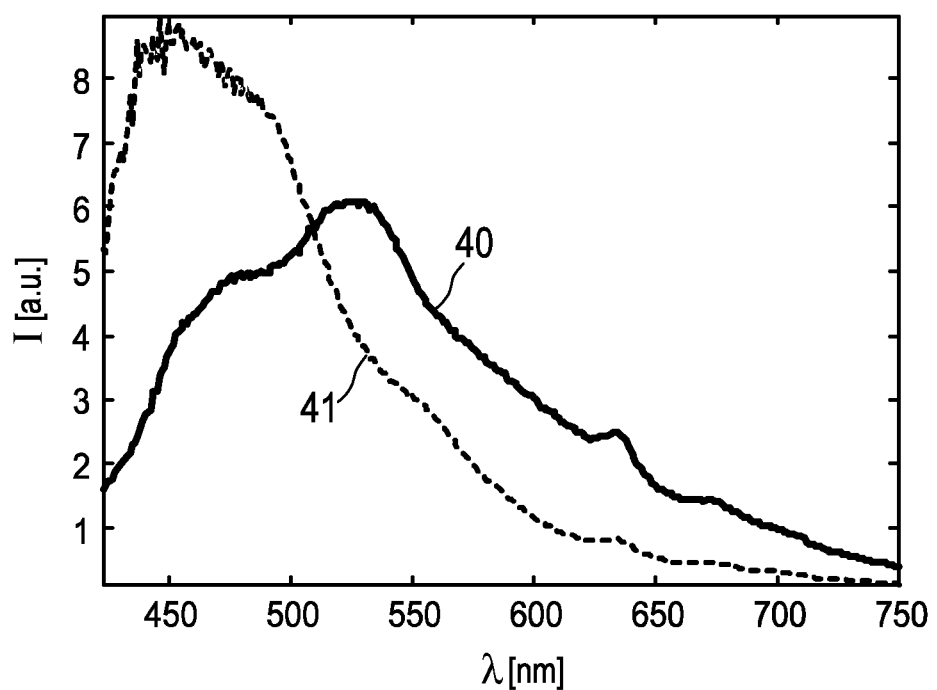
FIG. 7 shows exemplarily a measured fluorescence spectrum and an intrinsic fluorescence spectrum of human liver tissue.

FIG. 7 shows schematically and exemplarily a measured fluorescence spectrum 40 and an intrinsic fluorescence spectrum 41 of tissue being, in this example, human liver tissue. The intrinsic fluorescence spectrum 41 is only shown to illustrate the strong difference between the measured fluorescence spectrum 40 and the intrinsic fluorescence spectrum 41 at smaller wavelengths mostly due to blood absorption. The tissue state determination unit 5 is therefore adapted to ignore parts of the derivative of the spectrum, which correspond to wavelengths being smaller than 600 nm, but to base the determination of the state of the tissue on characteristics, in particular, peaks between 600 nm and 700 nm.

Figure 8:
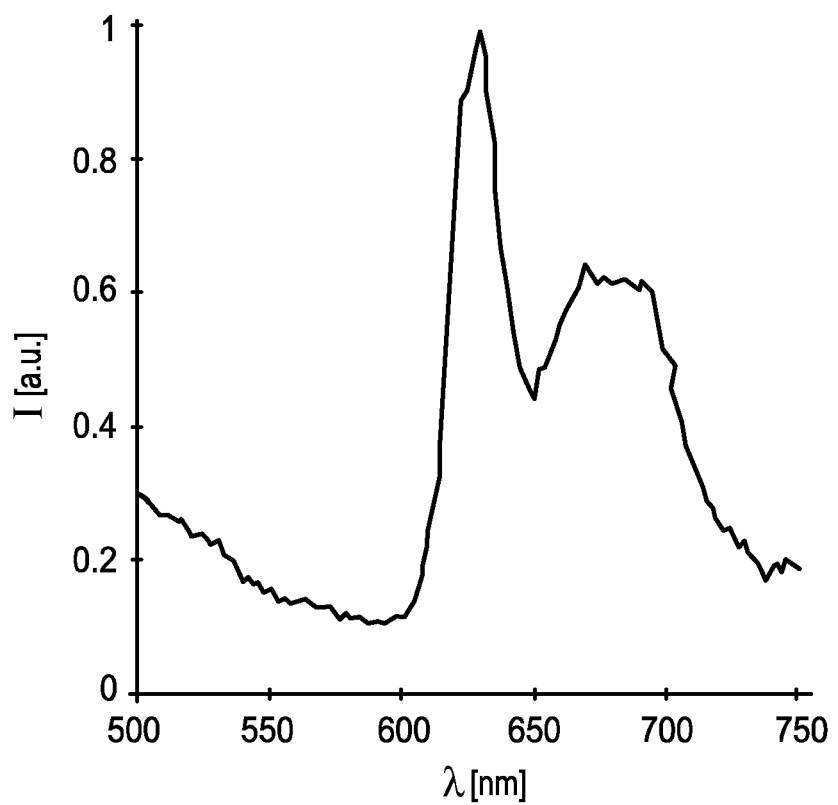
FIG. 8 shows exemplarily a fluorescence spectrum of Haematoporphyrin.

Healthy liver tissue contains a fluorophore F1 like Haematoporphyrin whose fluorescence spectrum is exemplarily shown in FIG. 8. It has a very sharp peak at 635 nm and a second broader one around 680 nm. In typical tissue measurements these peaks will be mostly obscured by other fluorescence peaks. It has been found that cancerous liver tissue contains a different unidentified type of porphyrin, which is denoted as fluorophore F2. This second fluorophore F2 has a main peak at 625 nm and a secondary peak around 690 nm. In this embodiment, this information about the different peak wavelengths of the respective fluorescence spectra of the respective fluorophores is sufficient for determining whether the liver tissue is healthy or cancerous, i.e. it is not necessarily required to have information about the full fluorescence spectrum of the individual fluorophores. In particular, information about the wavelengths of the main peaks of F1 and F2 can be sufficient.

Figure 9:
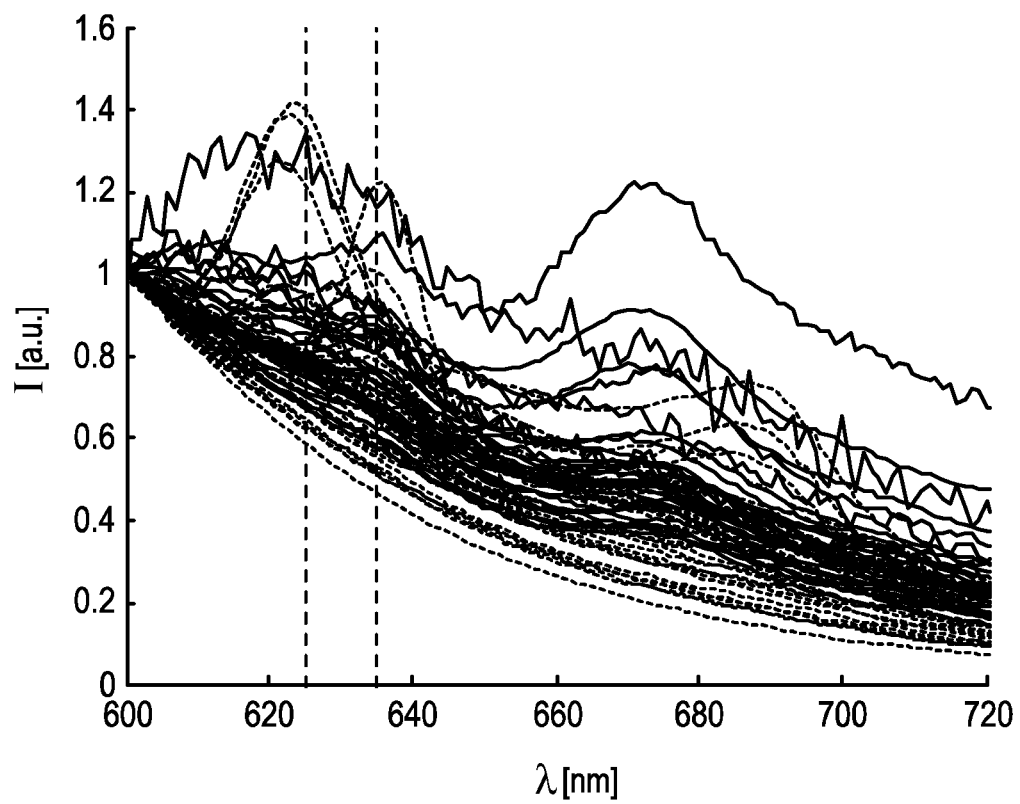
FIG. 9 shows exemplarily several fluorescence spectra of several human liver tissue samples.

FIG. 9 shows schematically and exemplarily several fluorescence spectra measured on human liver samples. The respective location, where the measurement was made, was classified by a pathologist as normal (solid lines) or cancerous (broken lines). Cancerous means, in this example, that either tumor or necrotic tissue was present in significant amounts, i.e. in 50% or more of the tissue at the respective location, while normal means that the tissue was free of tumor or necrotic tissue. The dashed bars at 625 nm and 635 nm denote maximum wavelengths of the main peaks. These wavelengths are preferentially the above mentioned first emission wavelength and the second emission wavelength. In FIG. 9, the graphs are scaled so that the fluorescent intensity I at 600 nm is one for all spectra.

Some of the spectra shown in FIG. 9 are very noisy. A few spectra clearly show the double peaks from Haematoporphyrin or from the unidentified second porphyrin. Most spectra show no visible peaks at all.

Figure 10:
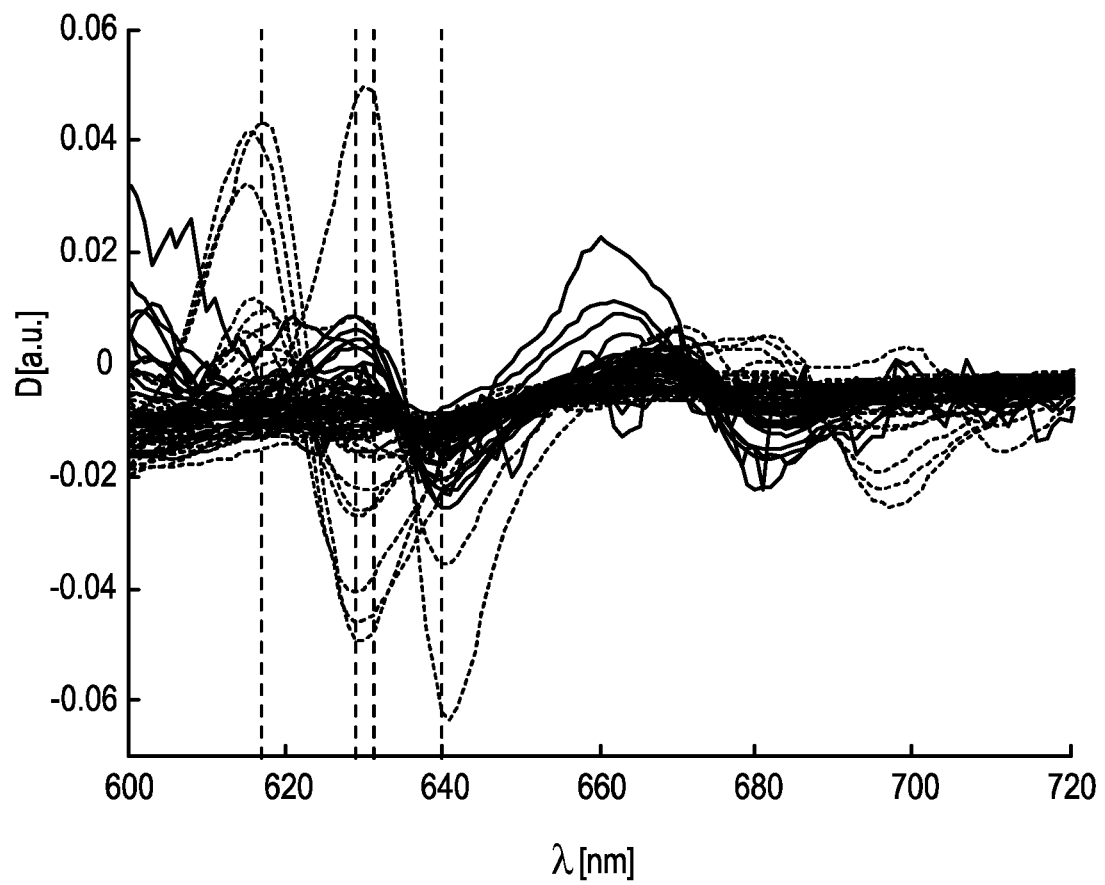
FIG. 10 shows exemplarily first derivatives of the spectra shown in FIG. 9.

FIG. 10 shows schematically and exemplarily first derivatives of the fluorescence spectra shown in FIG. 9, after these spectra have been smoothed. FIG. 10 clearly shows characteristics, which correspond to the fluorophores F1 and F2, at wavelengths at which these characteristics are not visible in the original spectra shown in FIG. 9. In FIG. 10, the dashed bars are at 617 nm, 629 nm, 631 nm and 640 nm.

In this example, the first measure y can be calculated by using following equation:

$$y=D(635\text{ nm}-6\text{ nm})-D(635\text{ nm}+5\text{ nm})-(D(625\text{ nm}-8\text{ nm})-D(625\text{ nm}+6\text{ nm})). \quad (1)$$

Thus, in this example, the first emission wavelength is 635 nm and the second emission wavelength is 625 nm. Moreover, the first measure does not depend on the entire respective part of the derivative of the spectrum, but only on some values of the derivative at certain emission wavelengths within the respective wavelength ranges, and the respective wavelength range around the respective emission wavelength can be regarded as being defined by the two respective wavelengths, at which the respective values, which are subtracted from each other, are present.

In this embodiment, the tissue state determination unit 5 is not only adapted to determine whether the tissue comprises the first state or the second state based on the first measure only, but in addition also on a second measure. For instance, to at least one of the first state and the second state a further emission wavelength of the emission light can be assigned, i.e. a further peak wavelength of the fluorophore F1 or the fluorophore F2 can be considered, wherein the tissue state determination unit 5 can be adapted to determine whether the tissue comprises the first state or the second state based on the first measure and based on a further measure that depends on a further part of the derivative defined by a further wavelength range around the further emission wavelength. Preferentially, the further measure does not depend on the entire further part, but only on some values of the derivative at certain emission wavelengths within the further wavelength range.

Preferentially, the tissue state determination unit 5 is adapted to determine also the further measure based on a difference between a) a value of the derivative of the spectrum at a wavelength, which is smaller than the respective further emission wavelength and within the respective further wavelength range, and b) another value of the derivative of the spectrum at a wavelength, which is larger than the respective further emission wavelength and within the respective further wavelength range. Thus, the further wavelength range can be regarded as being defined by the two wavelengths, at which the value and the other value of the derivative are present.

In the above described example of determining the state of liver tissue, the further emission wavelength can be 680 nm and the further measure can be defined in accordance with following equation:

$$x=D(680\text{ nm}-13\text{ nm})-D(680\text{ nm}+3\text{ nm}). \quad (2)$$

This further measure corresponds to a secondary peak of the fluorophore F1, whereas the first measure in accordance with equation (1) considers the main peaks of the fluorescence spectra of the fluorophores F1 and F2.

The tissue state determination unit 5 is preferentially adapted to comprise assignments between a) the first measure and optionally at least one further measure and b) the first state or the second state, and to determine whether the tissue comprises the first state or the second state based on the assignments and the first measure and optionally on the at least one further measure. The assignments and the measures, i.e. the wavelengths at which the values of the derivative of the spectrum are considered, can be determined by calibration measurements with many tissue samples having known states, wherein the assignments and the corresponding wavelengths are determined such that for as many tissue samples as possible the determined state of the respective tissue sample is similar to the known state of the respective tissue sample.

Figure 11:
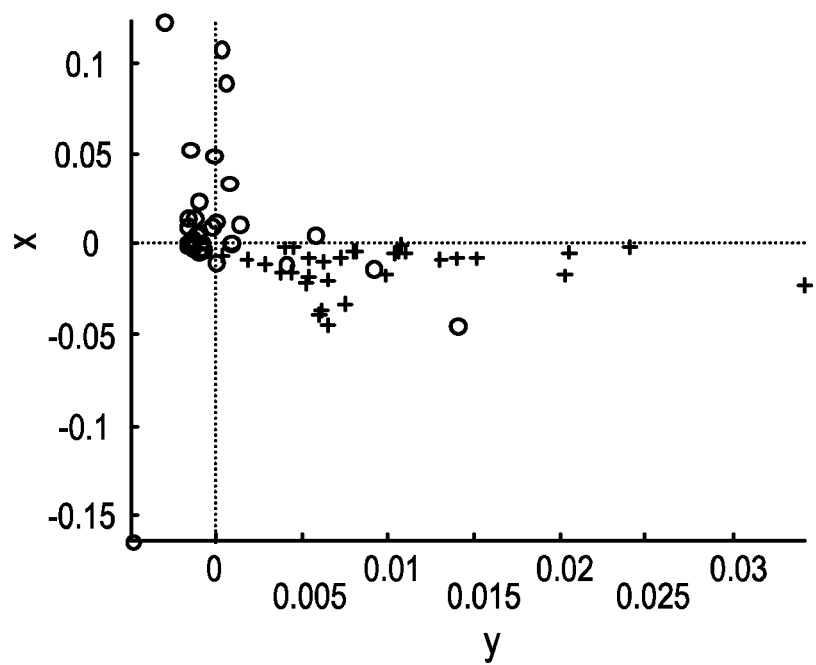
FIG. 11 shows exemplarily a plot of a first measure x and a second measure y in the case of human liver tissue samples.

FIG. 11 shows schematically and exemplarily a corresponding classification example. All normal samples can be correctly classified by checking for y≥0 and x≤0, wherein y denotes the first measure as defined above with reference to equation (1) and x denotes a further measure as defined above with reference to equation (2). In particular, FIG. 11, which is based on the graphs shown in FIG. 10, illustrates a possible classification between cancerous and healthy liver tissue. The crosses are measurements classified as normal, and the circles indicate samples classified as cancerous. All normal samples are in the lower right quadrant, while nearly all cancerous samples are outside of it. There are some cancerous samples which appear to be wrongly classified by this simple method, but this may indicate patches of healthy tissue in otherwise cancerous samples. Even taking these misclassifications into account, the overall classification result is very well. This is even though some of the measurements are very noisy in this example. In this embodiment, the tissue state determination unit can therefore be adapted to determine the state of the tissue based on the measures x and y and the assignments a) healthy, if y≥0 and x≤0, and b) cancerous otherwise.

In the above example, the operation of the detection apparatus has been described with respect of the determination of the state of liver tissue. In the following example, the operation of the detection apparatus will be exemplarily described with respect to the determination of the state of kidney tissue, in particular, with respect to the discrimination between healthy human kidney tissue and cancerous human kidney tissue.

Unlike liver tumors, kidney tumors contain a fluorophore F1 (most likely Haematoporphyrin) with a very sharp peak at 635 nm. Healthy liver contains a different unidentified type of porphyrin (F2) with a main peak at 620 nm. These emission wavelengths can be used to discriminate between healthy and cancerous human kidneys.

Figure 12:
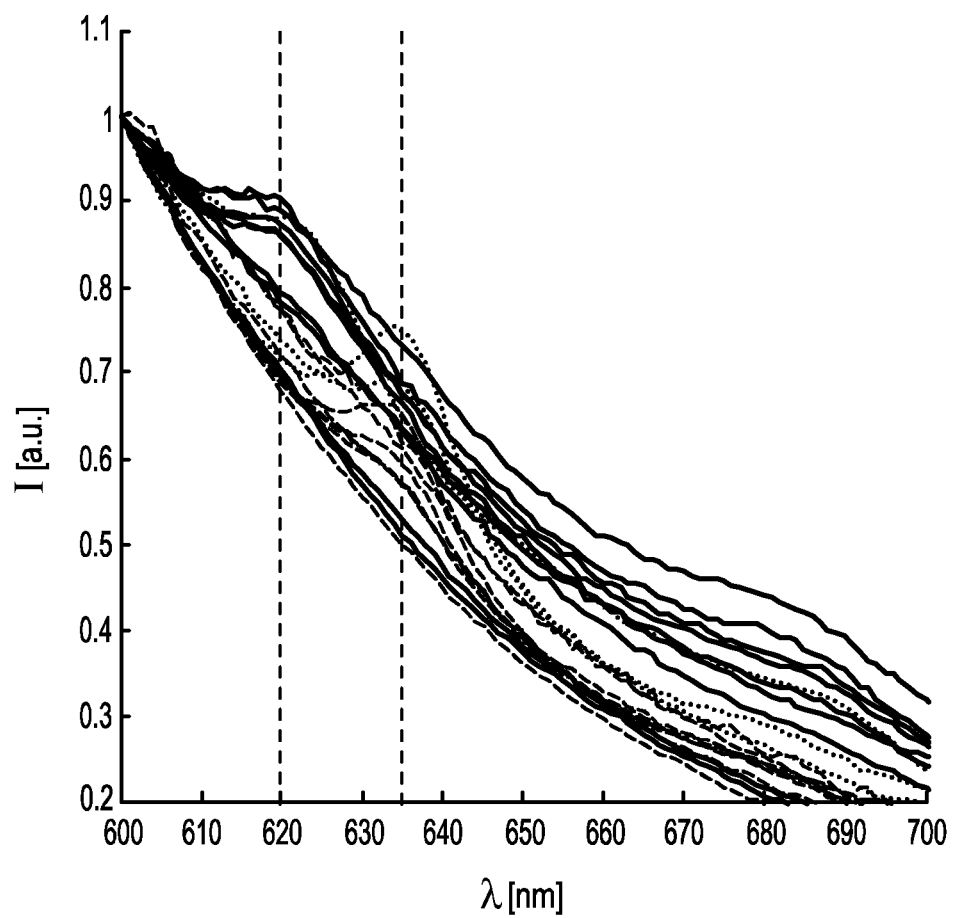
FIG. 12 shows exemplarily several fluorescence spectra of several human kidney tissue samples.

FIG. 12 shows exemplarily sample fluorescence spectra from 600 nm to 670 nm measured on human kidney samples. The solid curves are measured at locations which are classified as normal, i.e. healthy, the dashed curves are measured at locations which are classified as tumor, and the dotted curves are measured at locations which are classified as necrotic. The dashed vertical bars are located at 620 nm and at 635 nm and indicate first and second emission wavelengths. The curves are scaled such that the fluorescence intensity I at 600 nm is one for all fluorescence spectra. Most of the spectra show at least one noticeable bump in the spectral range from 600 nm to 670 nm. For normal spectra the maximum of this peak is around 620 nm, while for most tumor and necrotic spectra the maximum of the spectra is at about 635 nm. The lone necrotic sample with a bump at 620 nm is assumed to be due to a misclassification. There are however some spectra, which do not show a visible peak. The differentiation unit 4 generates therefore a first derivative of the sample fluorescence spectra, which are shown in FIG. 13.

Figure 13:
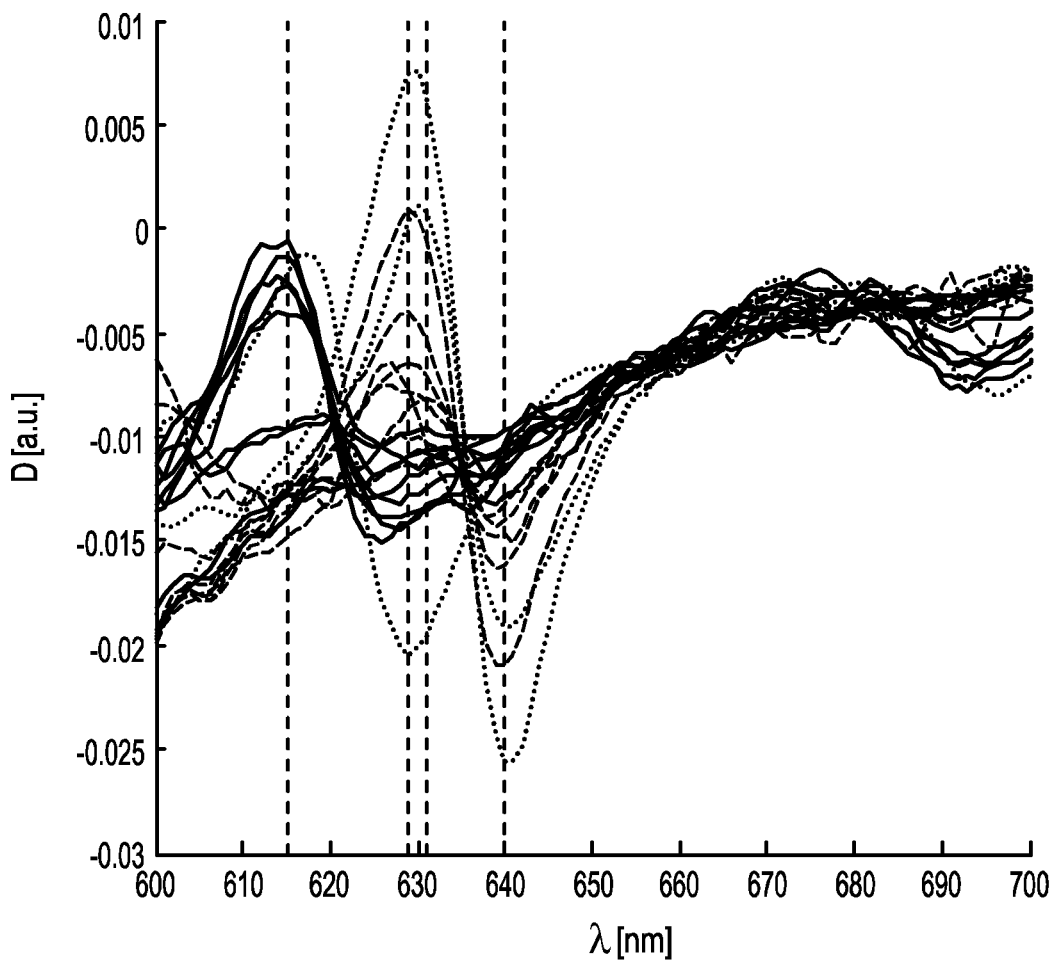
FIG. 13 shows exemplarily first derivatives of the fluorescence spectra shown in FIG. 12.

In FIG. 13 the vertical dashed bars are at 615 nm, 629 nm, 631 nm and 640 nm. In this embodiment, the tissue state determination unit 5 is adapted to determine the first measure v in accordance with following equation:

$$v=D(620\ nm-5\ nm)-D(620\ nm+11\ nm). \quad (3)$$

Moreover, the tissue state determination unit 5 is, in this embodiment, further adapted to determine a second measure in accordance with following equation:

$$w=D(635\ nm-6\ nm)-D(635\ nm+5\ nm). \quad (4)$$

If the first derivative is needed only at certain wavelengths as exemplarily described above with reference to equations (2) to (4), the fluorescence spectrum may comprise only some fluorescence intensity values at certain wavelengths, which are sufficient for determining the first derivative values as needed for determining the measures on which the determination of the state of the tissue is based. For instance, if a measure is based on two values of the first derivative at two wavelengths, in particular within a relatively narrow wavelength region, three fluorescence intensity values at three wavelengths can be sufficient, wherein a first wavelength is smaller than the wavelengths, at which the first derivative is needed, a second wavelength is between the wavelengths, at which the first derivative is needed, and a third wavelength is larger than the wavelengths, at which the first derivative is needed. Thus, the fluorescence spectrum may be a discrete spectrum having fluorescence intensity values at three or more wavelengths. The gaps between the different wavelengths are preferentially smaller than 10 nm.

Figure 14:
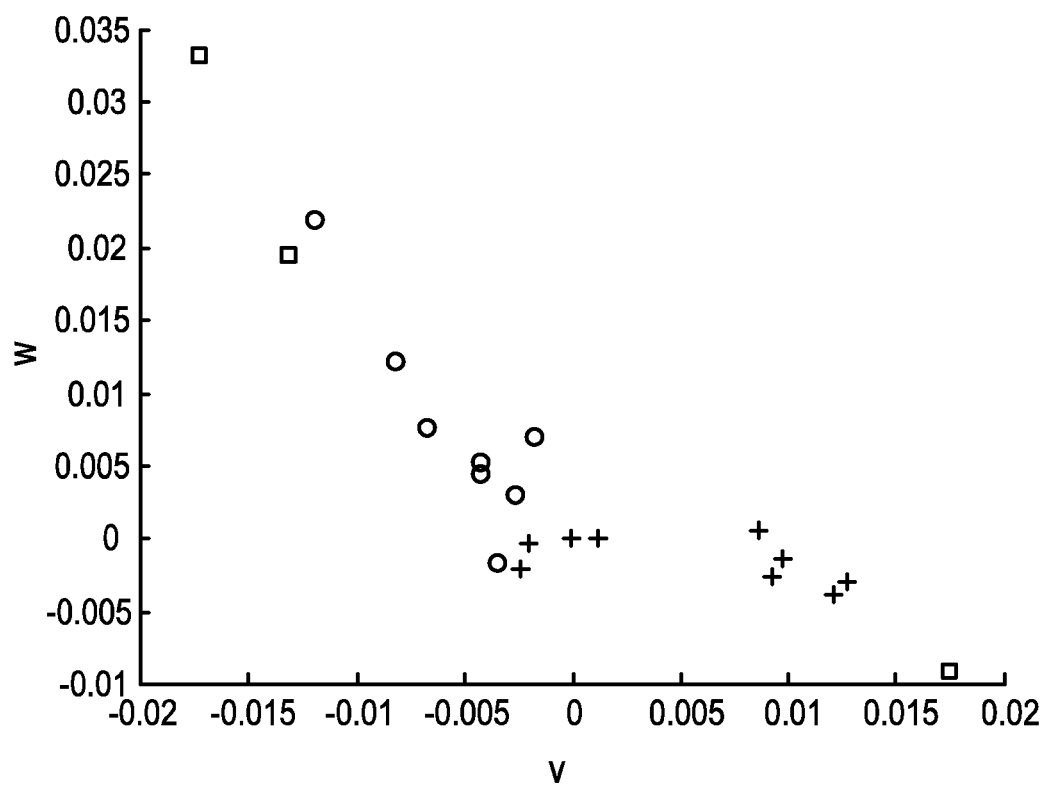
FIG. 14 shows a plot of a first measure x and a second measure y in the case of human kidney tissue samples.

FIG. 14 shows a plot of the v and w values for the kidney tissue samples. In FIG. 14, the crosses indicate measurements classified as healthy, the circles indicate measurements classified as tumor, and the squares indicate measurements classified as necrotic. With one exception, which is supposed to be caused by a misclassification, all healthy tissues are in the lower right corner in FIG. 14, while all necrotic and tumor tissues, which together define the kidney tissue samples in the cancerous state, are in the upper left corner. In this example, the tissue state determination unit 5 can therefore be adapted to determine the state of the tissue based on the first and second measures and based on assignments, which define that the tissue is healthy, if w<0 and v>−0.005, and otherwise cancerous defined as the group consisting of necrotic and tumor tissues.

Referring again to FIG. 1, the excitation light source is preferentially also adapted to illuminate the tissue via the optical fiber 28 with tissue type detection light and the emission light detector 3 is preferentially also adapted to detect the tissue type detection light from the tissue via the optical fiber 23. In this embodiment, the excitation light source 2 has therefore at least two functions, i.e. illuminating the tissue with tissue type detection light, in order to detect, which tissue, i.e. which kind of tissue, is illuminated, and illuminating the tissue with excitation light for allowing the tissue to emit fluorescence light, which can be used for determining the state of the tissue. The excitation light source 2 can therefore also be regarded as being a tissue type detection light source, and the combination of the excitation light source 2 and the optical fiber 28 can be regarded as being a tissue type detection illumination unit. In other embodiments, the excitation light illumination unit and the tissue type detection illumination unit can also comprise separate light sources providing the excitation light and the tissue type detection light, respectively.

The excitation light source 2 comprises, for example, a white light source with a wavelength selection means like a grating, wherein for exciting the tissue the wavelength selection means can be used for providing excitation light having a desired excitation wavelength and wherein for providing tissue type detection light the white light can be used for performing, for instance, diffuse reflectance spectroscopy (DRS). In another embodiment, also two light sources can be used, wherein one light source, for example, a laser provides the excitation light, and another light source like a white light source provides the tissue type detection light.

Since in this embodiment the emission light detector 3 is adapted to also detect tissue type detection light from the tissue, the emission light detector 3 can also be regarded as being a tissue type detection light detector, wherein the combination of the emission light detector 3 and the optical fiber 23 can be regarded as being a tissue type detection light detection unit. In other embodiments, the emission light detection unit and the tissue type detection light detection unit can be different units comprising different detectors.

In particular, the emission light detector can comprise an optical spectrometer in the visible wavelength range for measuring the fluorescence spectrum and, for example, the DRS spectrum. In another embodiment, for measuring the fluorescence spectrum a spectrometer being operable in the wavelength range between 600 and 700 nm can be used, and for measuring, for instance, the DRS spectrum, an additional spectrometer being operable in the near-infrared wavelength region can be used.

The use of DRS for detecting a tissue type is disclosed, for example, in the article "Epidural needle with embedded optical fibers for spectroscopic differentiation of tissue: ex vivo feasibility study" by Adrien E. Desjardins et al., Biomedical Optics Express, volume 2, number 6, pages 1453 to 1461 (2011), which is herewith incorporated by reference.

The detection apparatus 30 further comprises a tissue type providing unit 11 for detecting the tissue, of which the state is to be determined, i.e. to detect the type of the tissue, for instance, whether the tissue is kidney tissue or liver tissue, depending on the detected tissue type detection light. In particular, the tissue type detection light detection unit is adapted to generate a tissue type detection spectrum, wherein the tissue type providing unit 11 is adapted to compare the measured tissue type detection spectrum with stored known spectra of different tissue types, in order to determine the actual tissue type. Preferentially, characteristics like peak wavelengths of the actually measured tissue type detection spectrum are compared with stored peak wavelengths, which are assigned to different tissue types, in order to determine the actual type of the tissue, of which the state is to be determined.

The tissue state determination unit 5 is preferentially adapted to determine which first measure and which optional further measure has to be applied to the derivative of the fluorescence spectrum based on the detected tissue type. Thus, the tissue state determination unit 5 can comprise a storing unit, in which a first measure and optional further measures are assigned to different types of tissue, wherein the first measure and optional further measures to be applied in an actual measurement are determined based on the actually determined tissue type. The same detection apparatus 30 can therefore be used for determining the state of different types of tissue.

Referring again to FIG. 2, the electrode cap 27 of the cathode tip 20 is connected with a voltage source 13 via an electrical connection like a wire 29, in order to apply electrical energy to the tissue, if the tissue is in a cancerous state. For example, the voltage source 13, the electrical connection 29 and the electrode cap 27 can be adapted to perform a radio frequency ablation for ablating the cancerous tissue. The voltage source 13, the electrical connection 29 and the electrode cap 27 form a tissue modification unit for modifying the tissue by applying energy to the tissue. The energy application apparatus 1 further comprises a control unit 50 for controlling the different units of the energy application apparatus 1. The control unit 50 can be adapted to control the voltage source 13 depending on the determined state of the tissue. For instance, the control unit 50 can be adapted to control the voltage source 13 such that electrical energy is applied to the tissue only, if it has been determined that the tissue is cancerous.

In another embodiment, instead of a catheter a needle can be used. For example, a needle 201 having a tip as schematically and exemplarily shown in FIG. 15 can be used.

The needle 201 comprises optical fibers 223, 228 for illuminating the tissue with tissue type detection light and excitation light and for receiving absorbed, scattered and/or reflected tissue type detection light and emitted fluorescence light from the tissue. Moreover, at least one of the optical fibers 223, 228 or an additional optical fiber can be used for applying modification light to the tissue for modifying the same. For example, modification light can be applied to the tissue for performing a photodynamic therapy, wherein, for instance, porphyrin or another fluorophore is used as a photosensitizer. In this case, instead of the voltage source 13 a modification light source like a laser for providing modification light, which is delivered to the tissue via the needle 201, is used. The optical fiber of the needle, which is used for delivering the modification light to the tissue, and the modification light source form a tissue modification unit for modifying the tissue.

The detection apparatus 30 further comprises an x-ray fluoroscopy system 19 with an x-ray source 16 and an x-ray detector 17. The x-ray source 16 emits an x-ray beam 31 which traverses the part of the person 9, in which the catheter tip 20 is located. The x-ray beam, which has traversed the person 9, is detected by the x-ray detector 17. The x-ray detector 17 generates electrical signals depending on the detected x-ray beam and the electrical signals are used by a fluoroscopy control unit 18 for generating an x-ray projection image. The fluoroscopy control unit 18 is also adapted to control the x-ray source 16 and the x-ray detector 17. The x-ray source 16 and the x-ray detector 17 can be adapted to be rotatable around the person 9 for allowing the x-ray fluoroscopy system 19 to generate x-ray projection images in different directions. The x-ray fluoroscopy system 19 is, for example, a computed tomography fluoroscopy system or a C-arm fluoroscopy system. The generated fluoroscopy images can be provided, for instance, via the control unit 50, to a display unit 15 of the detection apparatus 30.

The fluoroscopy images can be used, for example, for navigation purposes. For instance, the catheter tip 20 can be navigated by using the navigation unit 14, while the location of the catheter tip 20 within the person 9 can be determined based on the fluoroscopy images. In other embodiments, other means for localizing the catheter tip 20 within the person 9 can be used. For example, the catheter tip 20 can be provided with location sensors, which allow determining the location of the catheter tip 20 within the person 9.

The navigation unit 14 is adapted to allow the catheter 8, in particular, the catheter tip 20, to be navigated to a desired location within the person 9. The navigation unit 14 can be adapted to allow a user to navigate the catheter 8 completely by hand or semi-automatically depending on a determined position and preferentially orientation of the catheter tip 20. The catheter 8 comprises built-in guiding means (not shown in FIG. 1), which can be controlled by the navigation unit 14. The catheter 8 can, for example, be steered and navigated by the use of steering wires in order to guide the catheter tip 20 to a desired location within the person 9.

The energy application apparatus 1 described above with reference to FIG. 1 can be regarded as being a combination of a detection apparatus and a tissue modification unit. Or, it can be regarded as a detection apparatus with integrated tissue modification means. For example, the tissue modification unit can be regarded as being formed by the voltage source 13, the electrical connection 29 and the electrode cap 27, wherein the other elements shown in FIG. 1 can be regarded as being elements of the detection apparatus.

Figure 16:
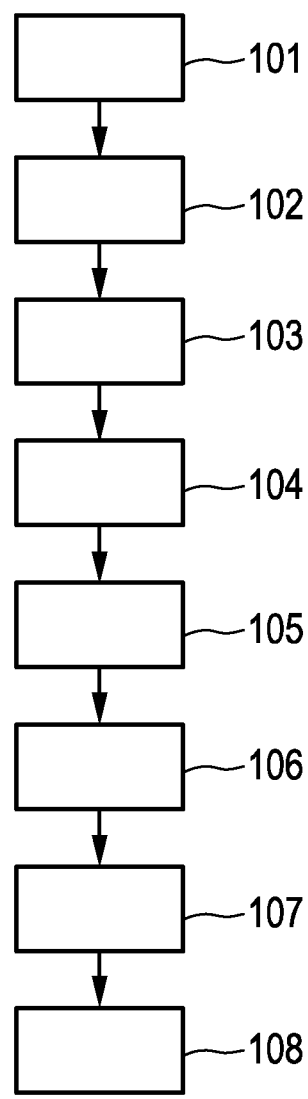
FIG. 16 shows a flowchart exemplarily illustrating an energy application method for applying energy to tissue.

In the following an embodiment of an energy application method for applying energy to tissue will exemplarily be described with reference to a flowchart shown in FIG. 16.

In step 101, the catheter tip 20 of the catheter 8 is navigated to a desired location within the person 9 based on fluoroscopy images provided by the fluoroscopy system 19 by using the navigation unit 14. For instance, the catheter tip can be navigated to the liver or to the kidney.

In step 102, the tissue 21 at the catheter tip 20 within the person 9 is illuminated by tissue type detection light, wherein the tissue type detection light from the tissue 21 is then detected for generating a tissue type detection spectrum. In step 103, the tissue type providing unit 11 determines the type of tissue, for example, whether the type is kidney tissue or liver tissue, depending on the tissue type detection spectrum.

In step 104, the tissue is illuminated by excitation light, wherein the wavelength of the excitation light can depend on the determined type of the tissue. In step 105, light emitted from the tissue, i.e. fluorescence light, is detected and a fluorescence spectrum is generated over a wavelength range of 600 nm to 700 nm. In step 106, the differentiation unit 4 generates a first derivative of the fluorescence spectrum, and, in step 107, the tissue state determination unit 5 determines the state of the tissue based on the first derivative. In particular, a first measure and optionally further measures are determined based on the fluorescence spectrum, and the state of the tissue is determined based on the first measure and the optional further measures. In particular, the first measure and the optional further measures can depend on values of the derivative of the fluorescence spectrum at certain wavelengths, wherein the respective measures can be provided by the tissue state determination unit 5 depending on the detected tissue type. In this embodiment, the tissue state determination unit 5 determines whether the tissue 21 is cancerous or not.

In step 108, the tissue 21 is modified by applying energy to the tissue 21, if in step 107 it has been determined that the tissue 21 is cancerous. In particular, via the voltage source 13, the electrical connection 29 and the electrode cap 27 a radio frequency ablation procedure is performed for ablating the tissue 21, if it has been determined that the tissue is cancerous.

Figure 15:
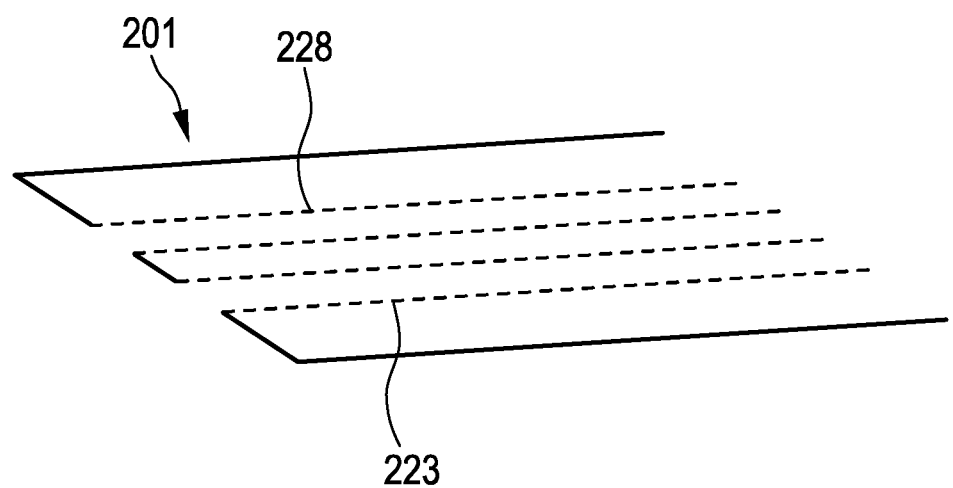
FIG. 15 shows schematically and exemplarily an embodiment of a tip of a needle.

If the needle shown in FIG. 15 is used instead of the catheter, in step 108 the tissue 21 can be illuminated with modification light for performing a photodynamic therapy, if it has been determined that the tissue 21 is cancerous, wherein, for instance, a fluorophore like porphyrin of the tissue can act as a photosensitizer.

In the above described embodiment of an energy application method for applying energy to tissue, the determination of the tissue type is optional. Thus, steps 102 and 103, and also the provision of the measures, on which the determination of the state is based, depending on a determined tissue type, are optional. For instance, based on the fluoroscopy images or another localization technique it can be known, in which part of the person 9 the catheter tip 20 is located and, thus, which type of tissue is in front of the catheter tip 20, and the detection apparatus can be adapted to a determination of the state of the tissue of the known type. In particular, the detection apparatus can be adapted to detect the state of only a single type of tissue, i.e. the detection apparatus can be adapted to determine the state of liver tissue or kidney tissue or of another type of tissue only.

Steps 102 to 106 can be regarded as being the steps of a detection method for determining the state of the tissue, wherein, as already mentioned above, the determination of the tissue type is optional, i.e. steps 102 and 103, and also the provision of the measures, on which the determination of the state is based, depending on a determined tissue type, are optional.

Fluorescence is the emission of light by a substance (called a fluorophore) that has absorbed light of a different wavelength. Biological tissues contain many different native fluorophores like collagen, elastin, flavin adenine dinucleotide (FAD), nicotinamide denine dinucleotide hydrate (NADH), tryptophan and porphyrins. The concentration of these fluorophores and their change over time can yield important information about the tissue state. For example, changes in the concentration (and therefore in the fluorescence) of NADH and FAD are directly related to changes in the metabolic processes of cells, while changes of collagen and elastin concentration indicate changes in the tissue structure.

Fluorescence spectroscopy can therefore be used to discriminate between different types of tissue or between healthy and abnormal tissue. It complements other optical spectroscopic techniques like diffuse reflectance spectroscopy (DRS) or Raman spectroscopy. Usually fluorescence spectroscopy is not used on its own but in combination with other optical techniques to improve specificity and sensitivity. However, with known apparatuses and methods, determining the concentration of single fluorophores from fluorescence spectra is difficult and often inaccurate.

Each fluorophore has a characteristic fluorescence spectrum i.e. it absorbs and emits light at characteristic wavelength ranges. By comparing or fitting a measured spectrum to the spectra of individual fluorophores information about the concentration of these fluorophores in the tissue can be gained. This is not straightforward, however, due to a number of problems.

First the measured fluorescence spectrum will be strongly distorted by scattering and absorption, both at the excitation and at the emission wavelengths. Therefore actual measured fluorescence spectra will often appear completely different from the superposition of the spectra of the individual fluorophores. As an example, FIG. 7 shows the difference between a measured fluorescence spectrum and an intrinsic fluorescence spectrum in a human liver.

As a consequence, quantitative information about fluorophore concentrations can usually only be gained, if correction techniques are used to compensate for the effects of scattering and absorption and to reconstruct the intrinsic fluorescent spectra of the tissue. The intrinsic fluorescence is the fluorescence that is only due to fluorophores without the influence of absorption and scattering.

While a multitude of techniques have been developed to recover the intrinsic fluorescence as disclosed, for example, in the article "A review of attenuation correction techniques for tissue fluorescence" by R. S. Bradley et al., Journal of the Royal Society Interface, volume 3, pages 1 to 13 (2006), they generally require additional measurements, usually either a diffuse reflectance measurement or a second fluorescence spectrum measured at a different geometry, and substantial computing power. In addition the various techniques for determining the intrinsic fluorescence spectra often disagree, introducing a substantial amount of error.

In the prior art, once the intrinsic fluorescence spectrum has been determined it can be fitted as a superposition of the emission spectra of individual fluorophores. However, this is hampered by two further issues. One is that the emission spectra of most mayor fluorophores are very broad and lack defining characteristics, in particular, they are basically Gaussian shaped. This allows for completely different combinations of fluorophores to produce nearly identical superposition spectra.

Moreover, the emission spectra of most fluorophores in tissue are not known, which make the situation in the prior art even worth. Instead generally a spectrum of a substance measured in a particular solvent is used. But spectra of the same fluorophore in different solvents differ from each other and from the spectra of the same fluorophore in tissue. In fact the same fluorophore may exhibit different emission spectra in different tissue types, because the chemical environment may be substantially different. To compound a difficult situation even further, many fluorophores can be divided into several subtypes, for instance, for collagen at least 29 subtypes are known. Last but not least reference spectra are often measured on fluorophores isolated from animal matter which may or may not be identical to fluorophores in human tissue.

As a result of these uncertainties literature sources strongly disagree about even the number of fluorophores that are needed to fit fluorescence curves of a given organ. Determining accurately the concentration of individual fluorophores from a measured spectrum is very difficult and involves a lot of guesswork.

The detection apparatus described above with reference to FIG. 1 allows the discrimination of healthy tissue from cancerous tissue based solely on fluorescence spectra. The corresponding discrimination method can be applied to the raw measurement data, i.e. it is not necessary to calculate an intrinsic fluorescence spectrum. Moreover, the discrimination method does not necessarily need prior knowledge about the spectra of individual fluorophores, because it does not attempt to determine the concentration of individual fluorophores.

The detection apparatus is preferentially adapted to measure the fluorescence spectrum of the tissue in a wavelength range that lies outside of strong absorption peaks. In particular, the fluorescence spectrum is preferentially measured in a wavelength range from 600 nm to 700 nm. This spectrum is then differentiated for determining a derivative of the spectrum.

The detection apparatus and the detection method use preferentially the assumption that in a first state the tissue comprises a first fluorophore F1 and in the second state the tissue comprises a second fluorophore F2. The two fluorophores comprise at least one sharp emission peak in the wavelength range, which lies outside of the strong absorption peaks, for excitation with excitation light. Both fluorophores are preferentially excited with the same wavelength. An emission peak is considered to be sharp, if it has a full width at half maximum (FWHM) with of less than 50 nm. It is further assumed that the peak wavelengths of the emission peaks of the different fluorophores significantly differ, wherein it is assumed that two peaks have significantly different peak wavelengths, if their peak wavelengths differ by at least 10 nm or at least a quarter of their FWHM. Fluorophore F1 has to be known to accumulate in the tissue, if the tissue is in the first state, and fluorophore F2 has to be known to accumulate in the tissue, if the tissue is in the second state. Such fluorophore pairs occur naturally in many relevant pairs of tissue states, for example, in healthy and cancerous liver tissue or in healthy and cancerous kidney tissue. In cases, in which no suitable fluorophores occur naturally or in which a higher contrast is desired, the fluorophores can be provided, for example, by injection, ingestion, et cetera.

Referring again to FIG. 1, the detection apparatus 30 can be regarded as comprising a probe 7 formed by the catheter 8 with the catheter tip 20 and a console 45 comprising several units of the detection apparatus like the light source and the detector. The emission light detector is a wavelength-selective detector, in particular, a spectrometer, in order to distinguish multiple fluorescence entities within the tissue and, thus, corresponding multiple possible states of the tissue. The excitation light source is, for example, a laser like a semiconductor laser, a light-emitting diode, a filtered light source like a filtered mercury lamp, et cetera.

In general, the wavelengths of the excitation light emitted by the excitation light source are shorter than the range of wavelengths of the fluorescence light that is to be detected. It is preferred that the excitation light detector comprises a filter for filtering out the excitation light, in order to avoid possible overload of the emission light detector by the excitation light.

Although in the embodiment described above with reference to FIGS. 1 and 2 the probe is a catheter, wherein optical fibers are used for transferring light from the console to the tissue and back from the tissue to the console, in other embodiments the probe can have another probe configuration, wherein this other probe configuration can be arranged within a catheter or for instance, in free space, in order to determine the state of the tissue on an outer surface of the person or in order to determine the state of a tissue sample, which has been separated from the person. FIGS. 17 to 22 show several possible probe configurations.

Figure 17:
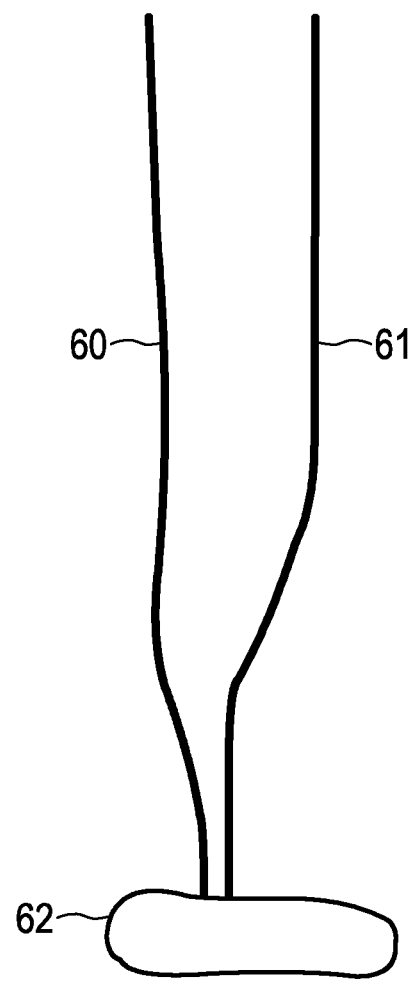
FIGS. 17 to 22 show several probe configurations, which can be used for illuminating the tissue with light and for detecting light from the tissue.

The probe configuration schematically and exemplarily shown in FIG. 17 uses a first optical fiber 60 for transferring light from a light source to the tissue 62 and a further optical fiber 61 for collecting light from the tissue 62 and for transferring the collected light to a detector. The probe configuration shown in FIG. 17 comprises therefore separate optical fibers, which can be used for excitation and detection, wherein these optical fibers may be in contact with the surface of the tissue or may penetrate the tissue when incorporated in a sharp probe like a needle.

Figure 18:
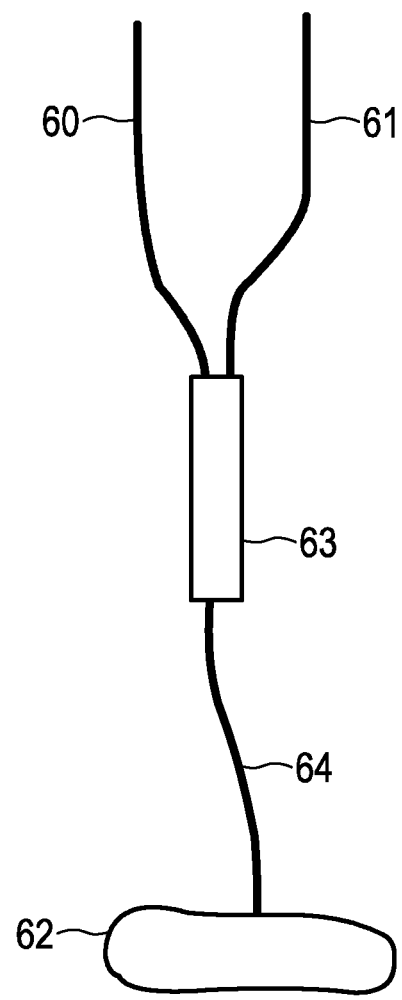

FIG. 18 shows schematically and exemplarily a further probe configuration comprising a first optical fiber 60 for guiding light of a light source to a fiber splitter 63, a second optical fiber 64 for guiding the light further from the fiber splitter 63 to the tissue 62 and for collecting light from the tissue 62, which is then transferred back to the fiber splitter 63, and a third optical fiber 61 for guiding the collected light from the fiber splitter 63 to a detector in the console. Also in the probe configuration shown in FIG. 18 the optical fiber 64 may contact, in particular, penetrate, the tissue 62.

Figure 19:
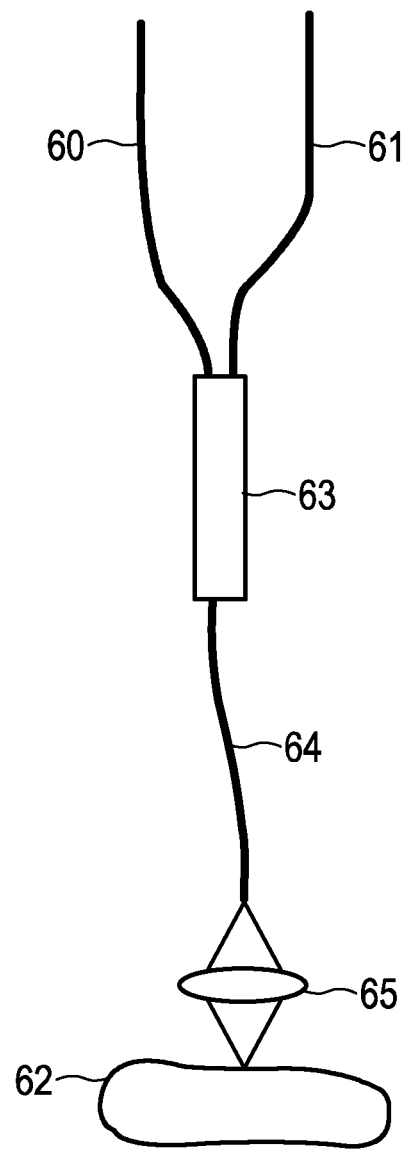

FIG. 19 shows schematically and exemplarily a further embodiment of a probe configuration, which differs from the embodiment shown in FIG. 18 in that a lens 65 is used for imaging the tip of the optical fiber 64 on the tissue 62. The probe configuration shown in FIG. 19 allows therefore a contactless determination of the state of the tissue.

Figure 22:
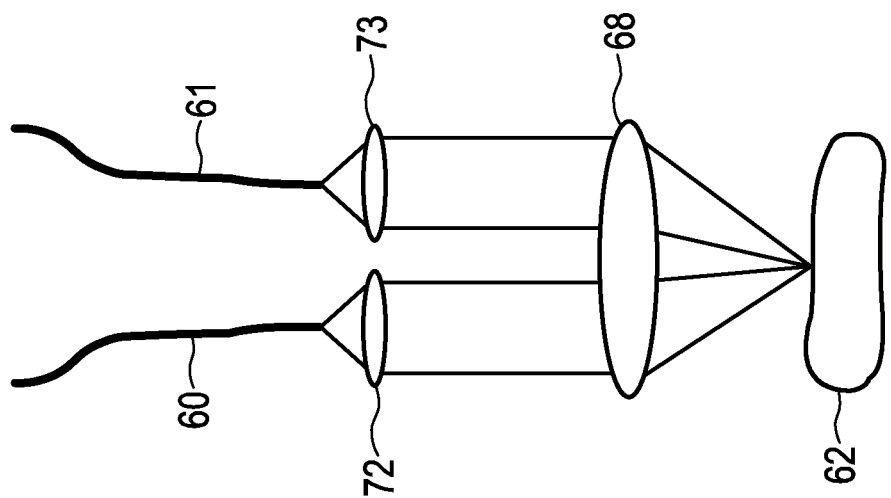
Figure 21:
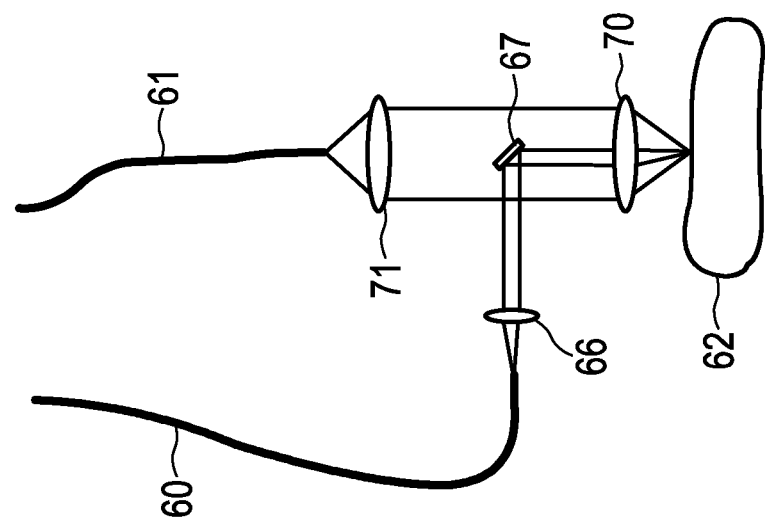
Figure 20:
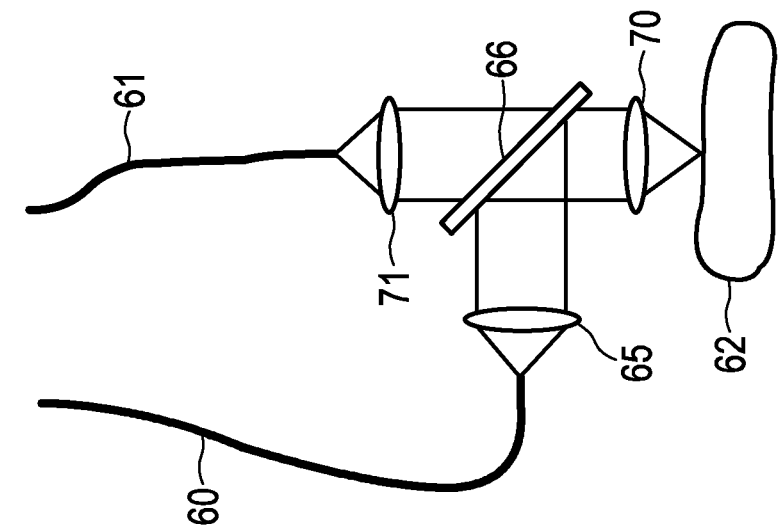

The probe configurations shown in FIGS. 20 to 22 use free-space optics to guide the light from the light source to the tissue and to collect the light from the tissue, which is then guided to the detector.

The probe configuration schematically and exemplarily shown in FIG. 20 provides a first light path for guiding light from a light source through a first optical fiber 60 and then via a first lens 65, a beam splitter 66 and a second lens 70 to the tissue 62 and a second light pass for guiding light from the tissue 62 via the second lens 70, the beam splitter 66, a third lens 65 and a second optical fiber 61 to a detector in a console. Because of the beam splitter 66 the two light paths are substantially separated. The beam splitter 66 can be, for example, a plate beam splitter or a beam splitter cube.

In the probe configuration schematically and exemplarily shown in FIG. 21, instead of the beam splitter 66 a small mirror 67 and a correspondingly small lens 66 are used for substantially separating the first light path from the second light path. In particular, the diameter of the mirror 67 and of the small lens 66 is smaller than the diameter of the expanded beam of the second light path.

FIG. 22 shows schematically and exemplarily a further possible probe configuration. In this probe configuration light from a light source, which is preferentially located in a console, is guided to the tissue 62 via a first optical fiber 60, a first smaller lens 72 and a second larger lens 68, thereby providing a first light path. A second light path for collecting light from the sample 62 and for guiding the collected light back to the detector is defined by the larger lens 68, a further smaller lens 73 and a second optical fiber 61. In this configuration the first and second light paths remain physically separated and overlap only at the measurement spot.

Optical filters, which are not explicitly shown in the figures, can be provided in the light path, which is used for illuminating the tissue, and/or in the light path, which is used for transferring light from the tissue to the detector. For instance, an illumination filter can be used, which improves the spectral purity of the illumination light. For instance, if the tissue should be illuminated by excitation light having one or several certain excitation wavelengths, the illumination filter can be used for filtering out light having wavelengths being different to the one or several excitation wavelengths. Such an illumination filter can be arranged, for example, between a beam splitting device and a light source. A detection filter can be inserted between a beam splitting device and a detector in order to, for example, attenuate unwanted light, which should not be detected, like excitation light to prevent overloading of the detector. Filtering functions can also be incorporated in the beam splitting device itself. For instance, the beam splitter 66 shown in FIG. 20 can be a dichroic beam splitter that reflects an excitation wavelength range, but transmits the wavelength range of fluorescence to be detected.

Although in an above described embodiment the type of the tissue is determined based on a spectroscopic measurement, the type of the tissue can also be determined in another way. For example, the fluoroscopy images or other localization information, which is indicative of the location of the probe within the person, can be used for determining the location of the probe within the person, wherein based on the location within the person it can be determined which type of tissue is located at the tip of the probe. For example, the tissue type providing unit can comprise a model of a person which describes at which locations within the person which tissue types are present, wherein the model can be registered with an actual image of the person, for instance, with a fluoroscopy image of the person, wherein the tissue type providing unit can determine the actual tissue type based on the actual location of the tip of the probe and the registered model.

Although in the above described embodiments certain tissue types are mentioned, the detection apparatus and the energy application apparatus can also be adapted to determine the state of tissue of another type. For instance, the detection apparatus and the energy application apparatus can be adapted to determine the state of cervix tissue or lung tissue, in particular, to determine whether cervix tissue or lung tissue is cancerous or not.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of the derivative of the spectrum, the state of the tissue, the tissue type, et cetera performed by one or several units or devices can be performed by any other number of units or devices. The determinations and/or the control of the energy application apparatus in accordance with the energy application method and/or the control of the detection apparatus in accordance with the detection method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a detection apparatus for determining a state of tissue. The detection apparatus comprises a fluorescence spectrum providing unit for providing a fluorescence spectrum of the tissue, a differentiation unit for generating a derivative of the fluorescence spectrum, and a tissue state determination unit for determining the state of the tissue from the derivative. This allows determining the state of the tissue, even if characteristics, which are related to the state of the tissue, are only hardly visible or not visible at all in the fluorescence spectrum. The reliability of determining the state of the tissue, for instance, whether the tissue is cancerous or not, can therefore be improved.

The invention claimed is:

1. A detection system for detecting a state of tissue, comprising:
   an excitation light source configured to generate excitation light for exciting the tissue;
   at least one fiber configured to guide the excitation light from the excitation light source to the tissue;

an emission light detector configured to generate a fluorescence spectrum from emission light emitted by the tissue in response to excitation by the excitation light; and at least one processor configured to:
define a first tissue state related to a first wavelength within a first wavelength range and a second tissue state related to a second wavelength in a second wavelength range,
generate a derivative of the fluorescence spectrum,
determine a first measure based on at least one of i) a first difference between a) the derivative at a wavelength which is smaller than the first wavelength and within the first wavelength range and b) the derivative at a wavelength which is larger than the first wavelength and within the first wavelength range, and ii) a second difference between a) the derivative at a wavelength which is smaller than the second wavelength and within the second wavelength range and b) the derivative at a wavelength which is larger than the second wavelength and within the second wavelength range, and
determine whether the tissue is in the first tissue state or the second tissue state based on the determined first measure.

2. The detection system of claim 1, wherein the first tissue state and the second tissue state are related to a wavelength in a wavelength range of 600 to 700 nm.

3. The detection system of claim 1,
wherein the first wavelength range is 630 to 640 nm and the second wavelength range is 620 to 630 nm.

4. The detection system of claim 1,
wherein at least one of the first tissue state and the second tissue state is related to a further wavelength, and
wherein the at least one processor is further configured to determine whether the tissue is in the first tissue state or the second tissue state based on the first measure and a further measure that depends on the fluorescence spectrum of the tissue at a further wavelength within a further wavelength range.

5. The detection system of claim 4,
wherein the at least one processor is further configured to determine the further measure based on a difference between:

a) the derivative at a wavelength which is smaller than the respective further wavelength and within the respective further wavelength range, and b) the derivative at a wavelength which is larger than the respective further wavelength and within the respective further wavelength range.

6. The detection system of claim 4,
wherein the further wavelength is within a range of 675 to 685 nm or within a range of 685 to 695 nm.

7. The detection system of claim 1,
wherein the at least one processor is further configured to provide a tissue type of the tissue and provide at least one of several predefined first measures depending on the provided tissue type.

8. The detection system of claim 7,
wherein the excitation light source is configured to illuminate the tissue with tissue type detection light; and
the emission light detector is configured to detect the tissue type based on the tissue type detection light.

9. The detection system of claim 1, wherein the tissue state is determined based on raw measurement data of the fluorescence spectrum of the tissue generated based on the emission light emitted by the tissue in response to excitation by the excitation light.

10. The detection system of claim 1, wherein the tissue state is determined without calculating an intrinsic fluorescence spectrum.

11. The detection system of claim 1, wherein the first tissue state corresponds to healthy tissue and wherein the second tissue state corresponds to cancerous tissue.

12. The detection system of claim 11, further comprising an ablation energy source configured to apply ablation energy to the tissue if the tissue has been determined to be cancerous tissue.

13. The detection system of claim 1, wherein the first tissue state is defined to correspond to a first measure being greater than or equal to a predetermined threshold value, and wherein the second tissue state is defined to correspond to the first measure being less than the predetermined threshold value.

* * * * *